United States Patent [19]

Herschler

[11] Patent Number: 4,477,469

[45] Date of Patent: Oct. 16, 1984

[54] PREPARATIONS CONTAINING METHYLSULFONYLMETHANE AND METHODS OF USE AND PURIFICATION

[76] Inventor: Robert J. Herschler, 3080 NW. 8th St., Camas, Wash. 98607

[21] Appl. No.: 277,592

[22] Filed: Jun. 26, 1981

Related U.S. Application Data

[62] Division of Ser. No. 71,068, Aug. 30, 1979, Pat. No. 4,296,104.

[51] Int. Cl.$^3$ ............................................. A61K 31/17
[52] U.S. Cl. ..................................................... 424/322
[58] Field of Search ......................................... 424/322

*Primary Examiner*—Stanley J. Friedman
*Attorney, Agent, or Firm*—Millen & White, P.C.

[57] ABSTRACT

Preparations containing methylsulfonylmethane (MSM) for administration to the skin, nails, other tissue and/or body fluids of a human or other animal subject are disclosed. Such compositions soften skin, strengthen nails and provide other benefits when applied topically. And, MSM compositions may also be administered orally, by injection and by inhalation.

In many instances, the effectiveness of MSM compositions is enhanced when such compositions contain carbamide (urea). Also, carbamide compositions are stabilized when they contain the MSM.

For topical administration, MSM compositions may be formulated in creams, lotions or gels which may be used alone or to serve as stable, neutral vehicles for other skin conditioning substances or therapeutically active drugs. Aqueous MSM solutions are suitable blood diluents.

25 Claims, No Drawings

PREPARATIONS CONTAINING METHYLSULFONYLMETHANE AND METHODS OF USE AND PURIFICATION

This is a division of application Ser. No. 071,068, filed Aug. 30, 1979 now U.S. Pat. No. 4,296,104.

BACKGROUND OF THE INVENTION

The present invention relates to compositions for conditioning the skin, nails, other tissue and/or body fluids of a human or other animal subject. More specifically, it relates to compositions which can be used to soften, smooth, lubricate and preserve the pliancy of human tissue, for reducing the brittleness of finger and toe nails, and as diluents for blood.

There presently exists a number of substances which are known to provide softening and other benefits to the skin when applied topically. The most popular of these is lanolin which is safe for topical applications and is used widely in cosmetic preparations.

To have a substantial effect, however, lanolin must be applied to the skin frequently and in large quantities. Even then, the softening effect on skin is less than has been obtained using lesser amounts of other skin softening substances. Compositions containing lanolin in sufficient quantity can leave the skin with a greasy feeling and may stain clothing if not thoroughly absorbed by the skin.

Due to the disadvantages of lanolin as a skin softener, substantial efforts have been made to find suitable alternative substances for skin conditioning. Unfortunately, most of the substances discovered have been synthetically derived and are not naturally occurring substances. Such substances are medically suspect and in some instances produce side-effects which make them unsuitable for use in cosmetics or other preparations for treating human tissue or body fluids.

One exception has been carbamide (urea) which is a naturally occurring substance in animals. Urea has been used with reasonable success for softening the skin and for treating skin diseases. Typically, the carbamide is applied in an aqueous solution or in the form of a cream. Such carbamide preparations have had only limited utility, however, because the carbamide tends to spontaneously decompose. As a result, preservatives for the carbamide must be added if such a skin treating composition is to have a reasonable shelf life.

The carbamide decomposition problem has been explored by a number of researchers. For example, Gunner P. E. Swanbeck has discovered various additives for stabilizing carbamide in a skin treating composition. In his U.S. Pat. No. 3,666,863, lactic acid is suggested as a preservative for skin treating compositions containing carbamide. And, in British Patent Specification No. 1,411,432, the same inventor describes a skin treating composition containing carbamide in combination with one or more salts selected from the group including sodium chloride, sodium thiosulfate and sodium dyhydrogen phosphate.

Even stabilized carbamide compositions of the type described in the Swanbeck references have their limitations. Most particularly, the effectiveness of urea as a skin treating agent is somewhat less than desired.

Another substance proposed for use in skin treating compositions is dimethyl sulfoxide (DMSO). As described in U.S. Pat. No. 3,549,770, DMSO has utility in relieving signs and symptoms of pain and tissue inflammation and for promoting tissue repair of a subject having a skin graft or suffering from burns or tissue damage. But, DMSO frequently causes adverse skin reactions so that DMSO has previously been considered unsuitable for use in cosmetics and other non-prescription preparations.

In general, it has been difficult to find substances which can be used to treat the tissues and body fluids of animal subjects without creating adverse side-effects. For example, after much research, dextran has become a widely accepted extender for blood plasma and is commonly used as a blood diluent. Despite the wide acceptance of dextran, this substance has a higher and more variable molecular weight than most normal blood constituents; and many subjects who receive the substancce react allergically. Other blood diluents have even greater drawbacks; so there is no universally accepted blood diluent or plasma expander.

SUMMARY OF THE INVENTION

It has now been discovered that compositions containing methylsulfonylmethane (MSM) can be used effectively to soften skin, to dilute blood, and for a variety of other useful purposes. MSM compositions are stable and safe for administration to human or other animal subjects and therefore eliminate many problems of the prior art. In particular, topically applied MSM compositions benefit the skin to a far greater degree than lanolin or carbamide. And, MSM can be combined with lanolin and/or carbamide to form skin preparations which are exceptionally effective.

MSM has proved to have varied and useful properties when applied to any animal tissue subject to undesired chemical bond formation including cross-linking. It has been observed to beautify the complexion, to enhance scalp and hair, and generally to help make the body of the user more flexible and comfortable. Various MSM formulations are also exceedingly useful as bland vehicles for pharmaceuticals.

Manicuring preparations can advantageously include MSM. Such preparations can increase nail toughness by reducing brittleness and can be used for softening cuticle for easy removal.

Depending on its intended use, a preparation can contain MSM in solution or in a dispersion. It may take the form of a cream, lotion, gel or paste for topical administration or a liquid, solid or vapor for administration by other routes such as injection, inhalation, oral injestion and the like.

The presence of MSM tends to stabilize compositions containing carbamide by inhibiting spontaneous carbamide decomposition. Similarly, carbamide stabilizes MSM in compositions so that MSM and carbamide are exceptionally well suited for use together.

Furthermore, DMSO may be included with certain MSM compositions to enhance their effectiveness. The adverse skin reactions frequently associated with use of DMSO, do not occur when certain of these MSM-DMSO compositions are used.

An aqueous composition, with the proper concentration of MSM, is an excellent diluent for blood. In such a composition MSM is nonallergenic, nonpyretic and has no interfering or undesirable pharmacological effect, even when administered in relatively large amounts for a blood diluent. MSM has a far lower molecular weight yet remains in the body longer than dextran.

MSM is a naturally occurring substance found in the tissues and body fluids of at least all higher animals. It can be isolated from mammalian milk, e.g. cow's milk. It is also a naturally occurring excretory product in higher animals, such as man, where it is found in the urine.

MSM is of exceedingly low toxicity to all forms of life, plant as well as animal. Except for its beneficial effect on animal tissue, it appears to be totally inert to the diverse chemical reactions involved in the processes of life.

MSM used in cosmetic preparations and other preparations administered to tissue and/or body fluids of a human subject should be substantially pure. Accordingly an improved process for purification of MSM has been developed.

It is an object of this invention to provide a composition suitable for application to the tissue of a human or other animal subject, which composition is safe and effective in softening, smoothing and/or comforting the skin or other tissue.

Another object is to provide such a composition that is stable over a long period of time so that it can be practically sold for use as a cosmetic or consumer skin care treatment.

A further object is to provide MSM compositions in a variety of forms and to provide a variety of methods of treatment with MSM in accord with the conditions or body parts to be treated. A particular related object is to provide such compositions in a viscous liquid form so that they can be easily applied topically and in an injectable liquid form so that they can be administered to subcutaneous tissue or body fluids.

It is also an object to provide a method of treatment to enhance moisture retention of the skin, relieve discomfort resulting from skin irritation and to soften, smooth and lubricate the skin.

Yet another object is to provide methods for treating connective tissue of a human or animal subject to resist cross-linking of collagen and other protein in the tissue and reduce dehydration or other alteration of cementing substrates such as hyaluronic acid.

An object is to provide a stable, neutral vehicle for pharmaceuticals, which vehicle has no interfering or undesirable pharmacological activity.

An additional object is to provide an effective composition and method for reducing the brittleness of finger and toe nails.

Also an object is to provide a method and composition for the softening of cuticle tissue so that it can be removed by gentle rubbing.

A specific object is to provide a safe and universally acceptable blood diluent.

Another object is to provide a method for purification of MSM to a purity at which it can be included in cosmetics or other preparations for administration to the tissue or body fluids of animal subjects.

These and other objects and features of the invention will be apparent from the following description.

DESCRIPTION OF PREFERRED EMBODIMENTS

Methylsylfonulmethane (MSM) is an active agent which can be used safely and effectively for treating human or other animal subjects. It can be administered by numerous routes for a variety of purposes.

Advantageously, MSM can be included in a cosmetic or other preparations applied to the skin. Such compositions, when applied topically, can beautify the complexion, improve the condition of the scalp and hair and help to make the body of the user more flexible and comfortable. Liquid cosmetic preparations can include MSM in aqueous or nonaqueous solutions or emulsions.

Compositions containing MSM may be in the form of an injectable liquid for subcutaneous application. For topical application, the composition will preferably be a solution or emulsion containing thickeners suitable to form a cream, lotion or gel. MSM can be administered in a mixture, e.g. a mixture of MSM crystals and peanut oil, which is surgically implanted or in a dry compound of body powders. It can be included in syrups, tablets or capsules which are ingested to preserve the pliancy of intestinal and other tissue. For application to lung tissue, MSM can be vaporized or dispersed in an aerosol for inhalation. Certain aqueous MSM compositions can be administered intravenously as nontoxic, nonallergenic blood diluents and modifiers of internal tissues.

A substantial advantage of MSM, regardless of how or why it is administered, is the noninteraction of MSM with the diverse chemical reactions involved in the process of life. Except for its inhibiting effect on cross-linking, MSM appears to be inert in the tissue and body fluids of living subjects.

Because of its inertness, MSM can be combined with non-irritating solvents and/or emulsifiers to provide excellent vehicles for pharmaceutical substances. Such vehicles deliver the pharmaceutical and simultaneously improve the condition of the subject's connective tissue. Inertness further makes MSM a superior substance for formulating aqueous blood diluent solutions as will be further described below.

To formulate MSM compositions, it is important to consider the physical properties of MSM. Commercially available MSM is an odorless, white, crystalline substance with a melting point of 109° C. and a boiling point of 238° C. It tends to sublime with heating. MSM has a molecular weight of 94.13, specific gravity of about 1.45 and an index of a refraction of 1.42 at 20° C.

The solubility characteristics of MSM are broad and somewhat unusual. These characteristics must be considered in preparing and using MSM compositions according to the present invention. MSM is highly soluble in hot water, but poorly soluble near the freezing point of water. For example, it is possible to dissolve over 1000 g. of MSM in 100 g. of water at 88° C., while only about 33.9 g. of MSM will dissolve in 100 g. of water at 26° C. MSM is soluble in a wide range of organic solvents and itself solvates many organic and inorganic compounds.

Preparations containing MSM in aqueous solution should generally contain only about 20 weight percent MSM and preferably no more than about 15 weight percent. Solutions containing MSM in greater concentrations can be formulated by using other pharmaceutically acceptable solvents, e.g. glycerine and/or ethanol. High concentration aqueous MSM compositions, suitable for certain specific purposes, can also be made by dissolving crystalline MSM in heated water immediately prior to application.

MSM also works well in emulsions such as those formed with a polymer of acrylic acid cross-linked with a polyfunctional agent. One suitable polymer is Carbopol 934P manufactured by B. F. Goodrich Chemical Company, Cleveland, Ohio. Other suitable emulsions can be formulated using modified cellulose polymers such as hydroxyethylcellulose.

When MSM is to be administered to human or other animal subjects it should be present in a composition which is pharmaceutically acceptable for the intended route of administration. In other words, the composition should not contain MSM in so great a concentration that it would be injurious; and the composition should not include unnecessarily toxic substances or substances which react with MSM to produce undesired substances.

a. MSM Administered to Connective Tissue

The reasons why MSM softens or otherwise benefits animal skin, are not fully understood. It is believed that a normal part of the aging process is the progressive cross-linking or bonding of protein such as collagen in animal connective tissue, especially skin. Such cross-links (possibly covalent, hydrophobic or hydrogen bonds and/or van der Waals associations) stiffen and harden the tissue. It appears that MSM acts to soften and preserve the pliancy of connective tissue by inhibiting bond structing of connective tissue, protein and other components in the tissue, and possibly by attacking existing cross-links. Thus, the benefits observed when MSM is used may result from reductions in dehydration of body substances such as hyaluronic acid and elastin, or from beneficial effects of MSM on fibrinogen.

The amount of MSM to be included in a particular composition may vary greatly depending upon the intended use of the composition. When treating the naturally soft and pliant skin of infants, a composition containing even minute quantities of MSM may be beneficial when applied to the skin. When treating the connective tissue of adult subjects, MSM should comprise at least about one weight percent of the composition administered. Disproportionately superior results are achieved using compositions containing at least about five weight percent MSM.

The maximum concentration of MSM in compositions for topical application is about 15 weight percent, preferably only about 10 weight percent. Greater amounts of MSM could, however, be used if the composition is heated and mixed prior to topical application.

The following examples are provided to illustrate the activity of MSM in softening, smoothing and otherwise inhibiting the aging of skin and other animal tissue and to show the noninteractivity which makes MSM suitable for use in vehicles for pharmaceutical substances and in blood diluents. The examples are not to be taken as an exhaustive list of the possible methods for using MSM and the benefits resulting from its use. The examples do, however, give some indication of the broad scope of this invention, specifically the suitability of MSM for a variety of purposes.

EXAMPLE 1

To determine the effectiveness of MSM in preserving the pliancy of animal connective tissue, young rabbits were sacrificed and bled. A portion of the vascular beds of these animals were removed and divided into three groups for testing. Those in the first group were infiltrated with a 10 weight percent solution of MSM in water. Those of the second group with a aqueous solution containing 10 weight percent each of MSM and carbamide. The third group was infiltrated with an isotonic saline solution.

After four hours, sections of the veins and arteries from the beds of each group were removed and immersed in a standard formaldehyde-based fixitive hardener solution of the type used to preserve tissue for histological study. After immersion for 20 minutes, the veins and arteries were removed from the hardening solution and examined. No hardening of the tissue was observed in the veins and arteries from the first two experimental groups. Vein and artery tissue from vascular beds of the third group displayed substantial hardening. From these results it appears that the MSM, with or without carbamide, prevented hardening of vein and artery tissue, apparently by blocking formaldehyde-induced cross-linking in connective tissue.

EXAMPLE 2

A series of tests were conducted to determine the effect of MSM on a hydrolized collagen representative of the collagen which is found in the exterior layer of animal skin and which hardens with dehydration.

Five aqueous solution of MSM were prepared, the solutions containing 2, 4, 6, 8 and 10 weight percent of MSM, respectively. Each of the solutions was heated and combined with a sample of modified collagen at a weight ratio of nine to one. Normally, collagen combined with heated water will swell and form physical and chemical bonds to form a gel. However, when the mixtures of this experiment cooled to room temperature, no gelatin had occurred in the mixtures containing 8 and 10 weight percent MSM solutions.

b. MSM and Carbamide Administered to Connective Tissue

A further discovery is that the addition of carbamide (urea) to an MSM composition enhances the effectiveness of the composition as a tissue treating agent, beyond expectations. Although carbamide is known to have some beneficial effects when applied to the skin, it is not believed that carbamide alone has any effect in inhibiting chemical bond linking of collagen.

Therefore in one embodiment, this invention relates to compositions comprising, in addition to MSM, an amount of carbamide effective to enhance the activity of the MSM, for example, those containing at least about one weight percent each of MSM and carbamide and preferably at least about five weight percent carbamide. In the examples hereinafter, compositions containing from one to 20 weight percent each of MSM and carbamide are described.

As will best be understood from the following examples, compositions containing both MSM and carbamide have a much greater activity in inhibiting bond structuring of substances in connective tissue than compositions containing either one of the substances along. It appears that the presence of carbamide aeceterates tissue penetration of MSM. Furthermore, experimental results show increased benefits beyond those expected to result from aeceterated MSM penetration alone.

In MSM compositions for application to the tissue of an animal subject, even small amounts of carbamide may be helpful in improving the overall softness of the skin. The composition becomes especially effective, however, when carbamide is present in an amount effective to multiply the activity of the MSM. Such a composition will contain at least about one weight percent carbamide and preferably at least about 5 weight percent.

EXAMPLE 3

The procedure of Example 2 was repeated twice. In the first repetition, 2, 4, 6, 8 and 10 weight percent aqueous carbamide solutions, instead of MSM solutions, were added to five collagen samples. When the collagen samples had cooled to room temperature, it was observed that carbamide had no effect in reducing collagen cross-linking in any of the mixtures.

In the second repetition, aqueous solutions containing equal weights of both MSM and carbamide were mixed with the collagen samples. A first solution contained 2 weight percent each MSM and carbamide, a second 4 weight percent each, a third 6 weight percent each, a fourth 8 weight percent each; and a fifth solution contained 10 weight percent of each.

When cooled to room temperature none of the collagen mixtures formed a gel except for the mixture containing first solution which had only 2 weight percent each of MSM and carbamide. This is in contrast with the procedure of Example 2 which showed no cross-linking inhibition using MSM solutions of less than 8 weight percent and the first repetition which showed no cross-linking inhibition by solutions containing carbamide alone.

Because cross-linking of collagen can so effectively be reduced by the application of MSM, and that the reduction can be increased by the addition of carbamide, such compositions can be administered to animal tissue to counter the cross-linking of collagen which is associated with aging and various disease processes. It specifically appears that the softness and pliancy associated with youthful, healthy skin thus can be maintained and that unhealthy, abused, old skin at least partially can be restored.

EXAMPLE 4

Sections of human cadaver skin were brought to a constant weight in a 50% relative humidity oven. The sections were divided into four groups. Each group of sections was immersed in a different aqueous solution as set forth in the following table:

| Group | Solution (aqueous) | |
|---|---|---|
| 1 | MSM | 10 wt. percent |
| 2 | Carbamide | 10 wt. percent |
| 3 | MSM | 10 wt. percent |
|   | Carbamide | 10 wt. percent |
| 4 | Isotonic saline | |

In each case, the sections were immersed for two hours, blotter dried and then stabilized at 50% relative humidity.

The cadaver skin, which can be expected to behave similarly to the outer layers of the epidermis of a healthy human, was found to retain less than 15% moisture when treated with the isotonic saline (Group 4) solution and then stabilized. The skin treated with solution containing MSM alone (Group 2) was substantially more flexible and retained 30-35% moisture. The highest moisture levels and greatest flexibility was observed in the sections which were treated with both MSM and carbamide (Group 3). The sections treated with the carbamide solution (Group 2) showed some improved moisture retention, but less than that of the Group 3 sections.

As this example illustrates, MSM may serve as an additive for embalming fluid to maintain tissue pliancy.

EXAMPLE 5

A variety of test applications were made to determine the effectiveness of compositions containing MSM and carbamide in treating human subjects having skin with a thickened stratum corneum.

A first solution containing 10 grams MSM, 45 grams water and 45 grams ethanol was applied three times daily to a human subject having skin with a thickened stratum corneum. After applications three times daily for a period of one week, a substantial softening and smoothing of the skin was observed.

A second solution containing 10 grams carbamide, 45 grams water and 45 grams ethanol was applied to a human subject having skin with a thickened stratum corneum. After one week, small improvements in skin pliancy were observed; but there was no increase in softness or smoothness of the skin.

A third solution containing 5 grams MSM, 5 grams carbamide, 45 grams water and 45 grams ethanol was applied to several human subjects having skin with a thickened stratum corneum. After a one week period of applications three times a day, the skin of these subjects was exceptionally soft and smooth in the areas of application. Even though the composition contained only 5 weight percent MSM, the extent of the physiological effect resulting from the application of this combined solution was greater than the effect which resulted from application of the first two solutions containing 10 weight percent MSM and 10 weight percent carbamide, respectively.

EXAMPLE 6

To determine the amount of MSM and carbamide needed to produce a desired effect, a series of tests on healthy skin of human subjects was performed. Eleven separate compositions were formulated containing different amounts of MSM and carbamide. As a solvent, each composition included a liquid comprising equal amounts, by volume, of water and ethanol.

Compositions were applied daily to separate subjects. And, the data was recorded for each subject when an increase in skin softness and smoothness was first detected. The results of this testing were compiled and appear in the following table:

| Composition | | |
|---|---|---|
| Wt. % MSM | Wt. % Carbamide | Result |
| 1 | 1 | Benefit seen in three weeks |
| 1 | 2 | Benefit seen in three weeks |
| 2 | 2 | Benefit seen in three weeks |
| 3 | 3 | Benefit seen in two weeks |
| 4 | 4 | Benefit seen in one week |
| 5 | 5 | Benefit seen in less than one week |
| 6 | 6 | Benefit seen in less than one week |
| 7 | 7 | Benefit seen in less than one week |
| 8 | 8 | Benefit seen in less than one week |
| 9 | 9 | Benefit seen in less than one week |
| 10 | 10 | Benefit seen in less than one week |

As can be seen from the table, softness and smoothness were improved when solutions containing even low amounts of MSM and carbamide were applied over a period of time. Specifically, it was found that a composition produced desirable effects at concentrations of MSM and carbamide of as low as 1 weight percent each. Rapid improvement in skin softness and smoothness were observed when the solution contained 5 or more weight percent each of MSM and carbamide.

EXAMPLE 7

Compositions containing MSM and carbamide improve the softness and pliability of skin even of persons suffering from adverse skin conditions. In one test, two human subjects suffering from "hide bound disease" or progressive systemic sclerosis were poorly responsive to standard treatments for softening the skin and making hands and feet more comfortable.

For treatment of the subjects, a preparation containing 20 weight percent MSM, 20 weight percent carbamide, 30 weight percent diamethyl sulfoxide and 30 weight percent water was prepared. A solution was formed by heating to about 40° C.

The subjects were treated by placing 15 milliliters of the solution in a plastic bag, placing a hand or foot to be treated in the bag. The hand or foot with plastic bag overwrap was then immersed in a heated water bath maintained at a temperature as warm as the subject would tolerate, taking care not to dilute the solution.

The hands and feet were thus immersed for 30 minutes, 3 times daily, for a period of 2 weeks. The result was a reduction in discomfort and an increased skin softness and pliancy.

Dimethyl sulfoxide was used in the solution to enhance penetration of MSM and carbamide into the effected tissue. No adverse side-effects resulted from administration of the DMSO.

EXAMPLE 8

Properly formulated compositions containing MSM and carbamide can be applied to skin which is injured or inflamed without causing adverse reactions.

A gel containing MSM and carbamide was made according to the following formulation:

| | |
|---|---|
| H$_2$O | 780 grams |
| carbamide | 80 grams |
| MSM | 50 grams |
| Carbowax 600 (PEG-12) | 50 grams |
| glycerin | 20 grams |
| Carbopol 940 (carbomer-940) | 4 grams |
| Na$_2$CO$_3$ (in 10 ml. of H$_2$O) | 0.25 grams |

This formulation was applied to the skin of subjects having a variety of adverse skin conditions including diaper rash, abrasions, wind burn, thermal burn and skin tears from berry bushes. In none of these applications did the subjects experience instantaneous discomfort of the type frequently encountered when medical preparations were applied. In a number of instances the preparation was soothing to the effected skin and provided a protective coating for the affected area.

EXAMPLE 9

It is found that MSM and carbamide can be used effectively in more complex compositions, such as the creams, lotions and gels which are most preferred for cosmetics preparations. One such formulation, a gel containing Carbopol 940 as a thickening agent, was made by combining the following ingredients:

| | |
|---|---|
| H$_2$O | 796 grams |
| carbamide | 80 grams |
| MSM | 50 grams |
| Carbowax 600 (PEG-12) | 50 grams |
| glycerin | 20 grams |
| Carbopol 940 (carbomer-940) | 4 grams |
| 2,2',2''-nitrilotriethanol | 1.75 grams |
| KOH | 0.25 grams |

Fifty human subjects applied the fomulation to the skin of the right hand and foot for three weeks on a morning and night (twice daily) routine. The gel was applied in sufficient amount to form a white matt film over the right hand and foot after which the excess gel was washed off with water. The subjects were requested to abstain from using other cosmetic preparations during the test period.

After one week, the evaluators noted a substantial improvement in skin softness, smoothness and comfort. Seven of the subjects continued to apply the formulation to the right hand and foot for a second week. At the end of this period, further improvements in softness, smoothness and comfort were observed.

EXAMPLE 10

MSM, alone or with carbamide, can also be added to a variety of cosmetic preparations other than skin lotions, creams and gels. For instance, a shampoo was formulated with the following ingredients:

| | |
|---|---|
| H$_2$O | 800 grams |
| MSM | 100 grams |
| carbamide | 100 grams |
| Carbowax 400 (PEG-8) | 50 grams |
| sodium lauryl sulfate | 100 grams |
| ammonium lauryl sulfate | 75 grams |
| cocamide MEA | 5 grams |

This shampoo formulation was tested both by subjects with healthy hair and scalp and by others with problems seborrheic dermatitis. Both groups found the shampoo to be effective, to leave the hair easily manageable and to soften the scalp. Those subjects having a dandruff problem found there was a reduction in itching, scaling and scalp inflammation after only four to five washings.

EXAMPLE 11

A hair styling gel including MSM and carbamide was prepared according to the following formulation:

| | |
|---|---|
| H$_2$O (with added ammonia) | 76 grams |
| polyvinylpyrrolidone (PVP) 45% aqueous solution | 6.0 grams |
| Carbopol 940 (carbomer-940) | 0.5 grams |
| MSM | 5 grams |
| carbamide | 5 grams |
| ethanol | 2 grams |
| Carbowax 600 (PEG-12) | 5 grams |

When applied to the hair of human subjects, this composition proved to be more effective in hair management than a comparable commercial product. Several subjects, having persistent itching scalp problem, observed a reduction in the itching. In two subjects dandruff was reduced.

EXAMPLE 12

Subjects used the gel described in example 8 as a pre-shave preparation with good results. If applied before retiring, or even minutes before shaving (using a commercial shaving cream), subjects obtained a more comfortable, smoother, and cleaner shave, using a blade razor, than if the commercial shaving cream was used alone. It also appeared that drag of the razor was reduced.

When the gel was used, leg hair was easily shaved without a commercial shaving cream overcoat. In all instances, use of the formulation left the skin feeling softer and smoother.

EXAMPLE 13

A nail conditioner was formulated from the following ingredients:

| | |
|---|---|
| $H_2O$ | 50 wt. percent |
| MSM | 10 wt. percent |
| carbamide | 10 wt. percent |
| glycerine | 5 wt. percent |
| dimethyl sulfoxide | 20 wt. percent |
| glyoxal (30% aqueous) | 5 wt. percent |

The formulation was applied with cotton pads to the nails of human subjects and allowed to remain for at least 15 minutes. At the end of that time, the nails were toughened, i.e. less brittle, and the cuticle was softened such that it could be removed by gentle rubbing.

It is not fully understood how the brittleness of the nail is reduced by application of the formulation. It appears, however, that the MSM may inhibit directional cross-linking in the nail. It may even break down naturally formed cross-links that are the cause of undesirably rigid structures responsible for nail brittleness.

The above composition is enhanced by the presence of 20 wt. percent dimethylsulfoxide (DMSO) which accelerates penetration of the MSM and carbamide into the nail. Subjects using this formulation had no reddening or irritation of the skin surrounding the nail. DMSO is an irritant to the epidermis of many people, so that the absence of adverse skin reactions was unexpected.

EXAMPLE 14

Nail polishes containing MSM were formulated by preparing 25 weight percent MSM solutions in ethyl or amyl acetate. Such solutions were mixed with the commercial nail polishes of several well-known U.S. manufacturers in such a ratio that the resulting mixtures contained about 5 weight percent MSM.

Nails of subjects using the resulting polish mixtures became less brittle with repeated applications. Also, the reformulated polishes were more easily removed with commercial nail polish removers than the original commercial polishes.

EXAMPLE 15

Reductions in nail brittleness were also observed when commercial nail polish removers, reformulated with MSM, were used repeatedly. Commercial nail polish removers containing esters, keytones and alcohols were combined with MSM in such amounts that the resulting mixtures contained 5–10 weight percent MSM. These proved to be beneficial in reducing nail brittleness.

C. MSM Administered Orally

EXAMPLE 16

To determine whether living animal subject would react adversely to orally administered compositions of MSM, a 40 weight percent solutions of MSM in distilled water was prepared. This solution was administered orally to laboratory rats at such a rate that each rat received 20 grams of MSM per kilogram of body weight per day.

After six weeks of administration, none of the animals had died or displayed unusual symptoms or behavior.

d. MSM in Vehicle Compositions

Because MSM is substantially inert to the chemistry of the body, compositions containing this substance are excellent vehicles for pharmaceuticals. When applied, the MSM will produce the desirable results mentioned above. MSM does not react with common pharmaceutical substances. And, as discussed below, MSM can actually stabilize certain substances such as carbamide so that the shelf life of certain pharmaceutical preparations can be extended by the inclusion of MSM.

EXAMPLE 17

The formulation of Example 9 was evaluated as a potential vehicle for agents known to have beneficial cosmetic, skin treating and/or insect repelling activities. A variety of compositions were made using the formulation of Example 9 as a vehicle.

In each instance, a 150 gram sample of the formulation described in Example 9 was combined, in a household, high sheer mixer, with 10 grams of an active agent and the resulting combinations thoroughly mixed. Combined formulations were made in this manner with each of the following agents:

propyl palmitate
hydrated lanolin
USP mineral oil
olive oil
peanut oil
thiabendazole solution (3% in DMSO)
erythromycin phosphate (10% in aqueous DMSO)
testosterone (5% solution)
triamcinolone (5% solution)
ethyl aminobenzoate (10% solution)
iodine (10% solution)
nicotinic acid (10% solution)
fluorouracil (2% solution)
vitamin A and vitamin D concentrates
disodium edetate
juniper tar (10% solution)
meta delphene (50% alcohol solution)

All of the compositions formed were stable. When applied to the skin, each composition produced the desirable tissue softening effects described in Example 9 without reducing the effectiveness of the agent. From this sampling it is logical to conclude that formulation of Example 9 could be very beneficial as a vehicle for a wide variety of pharmaceutical and cosmetic substances e. MSM-Carbamide Stabilization

An unexpected discovery resulting from experimentation with the above preparations was that compositions containing both MSM and carbamide are more stable than similar compositions containing MSM or carbamide alone, apparently because MSM and carbamide stabilize one another. MSM is thus useful as a stabilizer in almost any composition which contains the carbamide subject to spontaneous decomposition and vice versa.

EXAMPLE 18

To demonstrate the ability of MSM to inhibit the spontaneous decomposition of carbamide, laboratory tests were conducted. In these tests, the gel described in Example 8 was compared with a control formula that was an identical gel except that it contained no MSM. Multiple samples of each formula were placed in plastic coated metal tubes that were sealed and sapped.

Tubes containing each formulation were subjected to successive freeze-thaw cycles. The formulation without MSM began to break down to a liquid after two to three such cycles; while no break down of the composition including MSM was observed after ten freeze-thaw cycles.

Other tubes were maintained for two weeks in a dry oven at a temperature of 75° C. At the end of this time, gas pressure was elevated in the tubes containing formula without MSM such that the tubes were bloated and hissed upon opening. Gas in these tubes was determined by odor, to coat in ammonia which indicates that break down of the carbamide occurred. In tubes containing the formulation with MSM, no such gas pressure or ammonia odor was observed. MSM thus stabilized carbamide in the composition of Example 8 under accelerated aging conditions.

f. MSM in Blood Diluents

As discussed above, test applications of MSM have demonstrated only positive effects on human or other animal tissue. Its physical characteristics and inertness in normal bodily chemical reactions make MSM ideal for use in formulating diluents for body fluids such as blood. It is especially suitable as a plasma extender because subjects do not react allergically to MSM aas they do when dextran is used.

An MSM composition for use as blood diluent should be formulated as a solution which will create substantially the same oncotic pressure as normal plasma of the blood to be diluted. In such compositions, which primarily contain water and MSM, the MSM should comprise between 0.1 and 50 weight percent of the composition. Use of MSM amounts at the low end of this range presumes the presence of other dissolved substances which, together with the MSM, cause the solution to have substantially the same oncotic pressure as the body fluid to be diluted.

EXAMPLE 19

To determine the safety of intravenous administrations of MSM compositions for blood dilution and/or systemic treatment of collagen related diseases, MSM was dissolved in a standard 5 percent dextrose solution so that the resulting liquid composition contained 20 weight percent MSM. The composition was delivered intravenously to a dog weighing 9.5 kilograms at such a rate that the subject received 2 grams of MSM per kilogram of body weight per day.

The subject did not react adversely to the intravenous administrations and did not require physical restraint. After several weeks of this treatment there was no evidence of physical discomfort or injury to the subject.

g. Purification of MSM

A simple procedure may be used to obtain MSM of sufficient purity for use in compositions for treating the tissues of human or other animal subjects. MSM is combined with heated water to form a solution, the temperature of the water determining the amount of MSM which can be dissolved for purification. Activated charcoal is then added to the solution along with a substantially water insoluble base, such as aluminum or magnesium hydroxide, in an amount effective to neutralize the solution. The charcoal and base are then mechanically separated from the solution and the solution cooled to a temperature where purified MSM crystallizes. In most instances, crystals form when a solution is cooled to 10° C.; but enhanced crystallization occurs when the solution is cooled to below 5° C. The purified MSM crystals are then mechanically separated form the water. The remaining water still contains some dissolved MSM. Losses of MSM can thus be minimized by recycling the water for use as a solvent to purify additional MSM crystals according to this process.

EXAMPLE 20

In one such purification procedure, 400 grams of unpurified MSM were dissolved in 800 grams of heated water to form a solution. To the heated solution were added 10 grams of activated charcoal and four grams of magnesium hydroxide. The solution was then allowed to stand, with stirring, for 0.5 hours and then was filtered while still hot to remove the activated charcoal and magnesium hydroxide. The remaining solution, containing dissolved MSM, was chilled to below 10° C. to crystallize the MSM. MSM crystals were then separated by filtration and the resulting filtrate was heated and reused to dissolve additional MSM to be purified by the same process.

MSM produced by this process was extremely pure and thus suitable for use in any appropriate composition to be applied to human tissue or body fluids.

While I have described and given examples of preferred embodiments of my invention, it will be apparent to those skilled in the art that changes and modifications may be made without departing from my invention in its broader aspects. I therefore intend the appended claims to cover all such changes and modifications as fall within the true spirit and scope of my invention.

I claim:

1. A composition suitable for application to tissue and/or body fluids of a human or other animal subject comprising a pharmaceutically acceptable composition containing about one to twenty weight percent methylsulfonylmethane as an essential active agent, and an amount from about one to twenty weight percent carbamide effective to enhance the activity of the methylsulfonylmethane.

2. A composition as in claim 1 adapted for topical application and containing up to about fifteen weight percent carbamide.

3. A composition as in claim 2 comprising at least about five weight percent carbamide.

4. A composition as in claim 2 comprising: about 2 to about 10 weight percent methylsulfonylmethane, and about 2 to about 10 weight percent carbamide.

5. A composition as in claim 4 wherein the composition is a viscous liquid of the group including creams, lotions and gels.

6. A composition as in claim 5 wherein the composition is an injectable solution.

7. A composition as in claim 4 comprising methylsulfonylmethane in a gaseous medium.

8. A composition as in claim 1 further comprising up to thirty weight percent DMSO.

9. A composition for topical application to the skin of a human or other animal subject comprising an aqueous solution of one to ten weight percent each of methylsulfonylmethane and carbamide in a combined amount such that the composition is capable of eliciting a physiological effect upon application of the composition, the ratio of methylsulfonylmethane to carbamide being such that the extent of the physiological effect is greater than the extent of the effect which results from application of an otherwise identical composition containing only one of said methylsulfonylmethane and carbamide in an amount equal to said combined amount.

10. In a chemical composition containing carbamide, an amount of methylsulfonylmethane effective to retard decomposition of the carbamide.

11. A method for altering the condition of tissue and/or body fluids of a human or other animal subject comprising concurrently topically administering to the subject one to twenty weight percent methylsulfonylmethane and an amount of carbamide in the range of one to twenty weight percent effective to enhance the activity of the methylsulfonylmethane.

12. A method as in claim 11 wherein the carbamide is administered in a composition which includes the methylsulfonylmethane.

13. A method as in claim 11 wherein the carbamide is administered to the subject in a composition containing at least about five weight percent carbamide.

14. A method as in claim 11 wherein the methane and carbamide are administered to skin of the subject in an amount effective to enhance moisture retention of the skin.

15. A method as in claim 11 wherein the methane and carbamide are administered to skin of a subject suffering from irritation of the skin in an amount sufficient to relieve discomfort resulting from the irritation.

16. A method as in claim 11 wherein the methane and carbamide are administered to skin of the subject in an amount effective to soften the skin.

17. A method as in claim 11 wherein the methane and carbamide are administered to skin of the subject in an amount effective to increase the smoothness of the skin.

18. A method as in claim 11 wherein the methane and carbamide are administered to skin of the subject in an amount effective to preserve the pliancy of the skin.

19. A method as in claim 11 wherein the methane and carbamide are administered to skin of the subject, prior to shaving the skin with a razor blade, in an amount effective to reduce the drag of the razor during shaving.

20. A method as in claim 11 wherein the methane and carbamide are administered to connective tissue of the subject.

21. A method for treating finger and/or toe nails of a human or other animal subject comprising topically administering to the nails of the subject, an amount of a composition of claim 4 to effectively reduce the brittleness of the nails.

22. A method for removing cuticle from the finger and/or toe nails of a human or other animal subject, comprising topically administration to the cuticle, a composition of claim 4 in an amount effective to soften the cuticle so that it can be removed by gentle rubbing.

23. A method as in claim 12 wherein the methylsulfonylmethane and carbamide are administered as a pharmaceutically acceptable composition adapted for topical administration and containing up to 15 weight percent of methylsulfonylmethane.

24. A method as in claim 12 wherein the composition administered contains about 1 to about 10 weight percent each of methylsulfonylmethane and carbamide.

25. A method as in claim 12 wherein the composition administered also contains up to 30 weight percent dimethylsulfoxide.

* * * * *

UNITED STATES PATENT AND TRADEMARK OFFICE
CERTIFICATE OF CORRECTION

PATENT NO.   : 4,477,469
DATED        : October 16, 1984
INVENTOR(S)  : ROBERT J. HERSCHLER It is certified that error appears in the above-identified patent and that said Letters Patent is hereby corrected as shown below:

Claims 14-20, line 1 of each reads "A method as in claim 11 wherein the methane and"

line 1 of each should read: -- A method as in claim 11 wherein the methylsulfonylmethane and --

Signed and Sealed this

First Day of October 1985

[SEAL]

Attest:

Attesting Officer

DONALD J. QUIGG

Commissioner of Patents and Trademarks—Designate